United States Patent [19]

Termine et al.

[11] Patent Number: 4,880,862

[45] Date of Patent: Nov. 14, 1989

[54] FLAME RETARDANT ABS RESIN COMPOSITION

[75] Inventors: Enrico J. Termine; Nicolai A. Faystritsky, both of Lafayette; Dennis M. Borden, West Lafayette, all of Ind.

[73] Assignee: Great Lakes Chemical Corporation, West Lafayette, Ind.

[21] Appl. No.: 213,538

[22] Filed: Jun. 30, 1988

[51] Int. Cl.$^4$ ................................ C08K 5/06
[52] U.S. Cl. ......................... 524/373; 524/374
[58] Field of Search .................... 524/373, 374

[56] References Cited

U.S. PATENT DOCUMENTS

| | | | |
|---|---|---|---|
| 3,660,351 | 5/1972 | Schmidt et al. | 524/371 |
| 3,876,612 | 4/1975 | Anderson et al. | 260/45.75 |
| 3,883,479 | 5/1975 | Anderson et al. | 524/374 |
| 3,892,710 | 7/1975 | Anderson et al. | 260/45.75 |
| 3,971,758 | 7/1976 | Anderson et al. | 260/45.75 |
| 4,016,137 | 4/1977 | Anderson et al. | 260/45.75 |
| 4,016,139 | 4/1977 | Anderson et al. | 260/45.75 |
| 4,051,105 | 9/1977 | Anderson et al. | 260/45.75 |
| 4,059,561 | 11/1977 | Arai et al. | 524/371 |
| 4,171,330 | 10/1979 | Kyo | 524/371 |
| 4,567,218 | 1/1986 | Anderson et al. | 260/45.75 |

OTHER PUBLICATIONS

Hanbook of Plastics and Elastomers, Harper, Ed., McGraw Hill Publishing Company, 1975, pp. 1-68.

*Primary Examiner*—Veronica P. Hoke
*Attorney, Agent, or Firm*—Kirkland & Ellis

[57] ABSTRACT

Flame retardant ABS compositions incorporate an effective amount of halogenated unsymmetrical higher alkyl bisphenoxy alkane and an enhancing agent.

5 Claims, No Drawings

FLAME RETARDANT ABS RESIN COMPOSITION

BACKGROUND OF THE INVENTION

1. Field of the Invention

The present invention relates to a non-blooming flame retardant ABS resin composition and more particularly to an ABS resin composition incorporating halogenated unsymmetrical higher alkyl bisphenoxy alkanes.

2. Description of the Art

Traditionally, most flame retardants, although efficient in their function of retarding the rate of combustion in a resin system, have a tendency to affect adversely one or more key properties of the resin. For example, many flame retardant additives tend to reduce impact strength of the resin; to migrate from the resin composition resulting in a phenomenon known as "bloom"; to plasticize the resin composition adversely, thus lowering the heat deflection temperature; or to degrade when exposed to indoor and outdoor light.

It is, therefore, essential that flame retardant agents be specifically tailored to the resin system so that in addition to their role as flame retardants, they will also enhance the desirable characteristics of the resin composition. Those skilled in the art well know that the selection of such an application specific flame retardant is unpredictable at best. Therefore, even if a given agent may exhibit utility in a particular resin system, there is no guarantee that this agent will have any use at all with other resins.

Acrylonitrile-butadiene-styrene ("ABS") thermoplastics offer a good balance of physical and mechanical properties such as good abuse resistance, heat resistance, moldability, stain resistance, chemical resistance and surface hardness. Typically ABS thermoplastics are used in a wide variety of applications because of their properties and moderate costs. For example, ABS thermoplastics are used by telephone equipment, electronic, and automotive manufacturers who require materials of high impact strength.

ABS thermoplastics are derived from acrylonitrile, butadiene and styrene. Some of the properties of typical ABS resins are described on pages 1-68 of Harper's Handbook of Plastics and Elastomers" published by McGraw-Hill Book Company in 1975.

A number of flame retardants have been described for ABS resins in the art. For example, the following materials have all been used in various ABS systems: bis(tribromophenoxy)-ethane, bis(pentabromophenoxy)-ethane, octabromodiphenyl oxide, decabromodiphenyl oxide, tetrabromobisphenol-A, bis(tribromophenoxyethyl)-tetra bromobisphenol A ether. Among the prior art specifically dealing with flame retarding ABS resins are U.S. Pat. No. 4,016,139; and U.S. Pat. No. 4,567,218, and the references cited therein.

The foregoing flame retardant agenst for ABS plastics have not been entirely satisfactory because of problems of bloom, thermal migration, heat instability, ultraviolet light instability, discoloration, or adverse effects on properties such as impact strength and flowability.

Many applications of ABS resins with flame retardant agents require that certain key properties be maintained. Examples of key properties include impact strength, light stability and retention of surface aesthetic properties. In particular, manufacturers of computer housings desire a thermoplastic ABS resin which is flame retardant, light stable, and resistant to bloom.

It is well known in the art to use various bromine containing compounds as flame retardant agents. The compositions obtained using these various bromine containing compounds have a tendency to change color on exposure to light, to develop a reduction in surface gloss, and to form deposits of flame retardant agents on the polymer surface.

Anderson, et al., U.S. Pat. No. 3,876,612 disclose ABS plastic compositions containing symmetrical bisphenoxy flame retardants. The compositions of the flame retardants are depicted by the following formula:

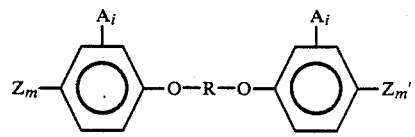

where Z is bromine or chlorine; m and m' are integers having a value of 1-5; and i and i' are integers having a value of 0-2; A is a cyano, nitro, lower alkoxy, lower alkyl, fluorine, dialkylamino, phenyl, halo-phenyl, benzyl or halo-benzyl group; and R is chosen from the following group:

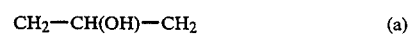  (a)

  (b)

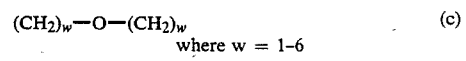  (c)

where w = 1-6

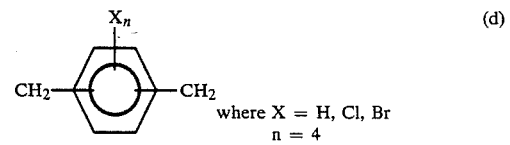  (d)

where X = H, Cl, Br
n = 4

$CH_2-C(O)-CH_2$  (e)

  (f)

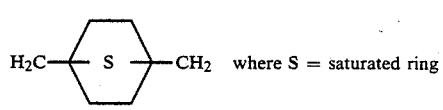  (g)

where S = saturated ring

Anderson, et al., '612 does not disclose the use of an unsymmetrical higher alkyl bisphenoxy alkane as a flame retardant agent for the disclosed ABS resin.

U.S. Pat. No. 3,883,479 issued to Anderson, et al., discloses plastic compositions containing ABS and symmetrical bisphenoxy compounds. The bisphenoxy compounds have the formula:

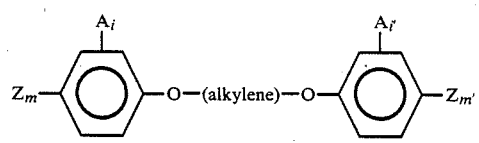

wherein A is bromine, m and m' are integers having a value of 1-4, i and i' are integers having a value of 1 or 2. The alkylene is a straight or branched chain alkylene group having from 1 to 6 carbon atoms. A is to be selected from the group consisting of cyano, nitro, lower alkoxy, lower alkyl (defined as $CH_3$, $C_2H_5$, $C_3H_7$ or $C_4H_9$), fluorine, dialkylamino, phenyl, halo-phenyl, benzyl or halo-benzyl group. Anderson, et al., '479, do not disclose the use of an unsymmetrical higher alkyl bisphenoxy alkane as a flame retardant agent.

Anderson, et al., U.S. Pat. No. 3,892,710 disclose ABS plastic compositions containing symmetrical halogenated aryl flame retardants. The flame retardants have the formula:

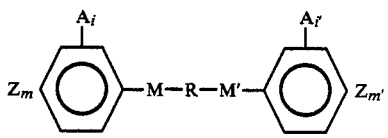

where Z is bromine or chlorine; m and m' are integers having a value of 1–5, i and i' are integers having a value of 0 to 2, M and M' are each independent and are from the group consisting of oxygen, nitrogen or sulfur as long as both m and m' are not oxygen. A is chosen from the group consisting of cyano, nitro, lower alkoxy, lower alkyl, fluorine, diakylamino, phenyl, halo-phenyl, benzyl or halo-benzyl group. Anderson, et al., 'b 710's disclosure on halogenated aryl flame retardants fails to suggest usage of an unsymmetrical higher alkyl bisphenoxy alkane.

In U.S. Pat. No. 3,971,758, Anderson, et al., disclose an ABS plastic composition containing symmetrical bisphenoxy flame retardant compounds. The compositions of the flame retardants have the formula:

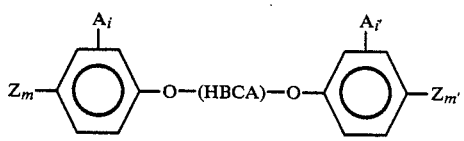

where Z is bromine or chlorine; m and m' are integers having a value of 1 to 5; i and i' are integers having a value of 0 to 2; HBCA is a halo-branched alkylene group having from 1 to 6 carbon atoms; and A is cyano, nitro, lower alkoxy, lower alkyl ($C_1$-$C_4$), fluorine, dialkylamino, phenyl, halo-phenyl, benzyl or halo-benzyl group. Again, Anderson, et al., '758 fail to disclose usage of an unsymmetrical higher alkyl bisphenoxy alkane as a flame retardant agent.

Anderson, et al., U.S. Pat. No. 4,016,137, describe plastic compositions containing ABS and symmetrical bisphenoxy flame retardant compounds, which have the following formula:

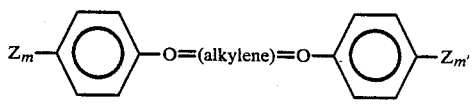

where Z is bromine, m and m' are integers having a value between 1 and 5 and the alkylene is a straight or branched alkylene group containing 1 to 6 carbon atoms. This reference again fails to suggest usage of an unsymmetrical higher alkyl bisphenoxy alkane as a flame retardant.

Anderson, et al., U.S. Pat. No. 4,016,139 disclose a composition containing an ABS polymer, a symmetrical bisphenoxy flame retardant and a flame retardant enhancing agent. The bisphenoxy flame retardant has the following formula:

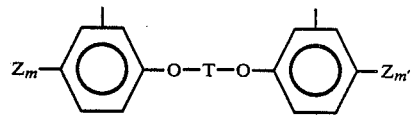

wherein Z is bromine, m and m' are integers having a value of 1 to 5 so that the total bromine atom content ranges from 6 to 10 atoms, and T is a straight chain or branched chain carbon group having 1 to 4 carbon atoms. There is a lack of disclosure of a unsymmetrical higher alkyl bisphenoxy alkane compound in Anderson, et al., '139.

Anderson, et al., U.S. Pat. No. 4,051,105, disclose a plastic composition. The plastic composition contains an ABS polymer and a symmetrical b isphenoxy compound having the formula:

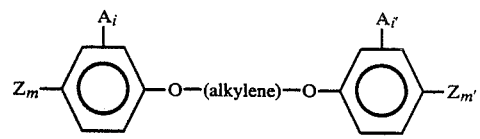

where Z is bromine, m is an integer having a value of 1 to 5, and m' is an integer having a value of 0 to 4, i is an integer having a value of 0 to 2, and i' is an integer having a value of 1 to 5. The alkylene is a straight or branched chain alkylene group having from 1 to 6 carbon atoms and A is chlorine. Clearly there is no disclosure of unsymmetrical higher alkyl bisphenoxy compound in Anderson, et al, '105.

In overview, the bromine containing compounds for ABS resin described by the Anderson, e al., patents disclose the usage of symmetrical bisphenoxy alkane compounds containing nuclear aromatic bromination, alkylation and various other substitutions. The use of these symmetrical bisphenoxy alkane compounds has not been entirely satisfactory in ABS systems. In particular, the symmetrical bisphenoxy compounds such as bis(tribromophenoxy)-ethane tend to bloom or migrate to the polymer surface is ABS systems.

Accordingly, a primary object of the present invention is to provide an agent capable of flame retarding ABS resin compositions without exhibiting problems of bloom, heat or light instability, or any of the other disadvantages of the prior art ABS flame retardant agents.

A further object is to provide flame retardant ABS resin compositions that exhibit the desired level of flame retardancy without suffering any deterioration of physical properties.

Yet a further object is to utilize an halogenated unsymmetrical higher alkyl bisphenoxy alkane, as flame retardant agents for ABS resins.

SUMMARY OF THE INVENTION

The foregoing and other objects, advantages and features of this invention may be achieved with flame retardant ABS resin compositions comprising a normally combustible ABS resin; an effective amount of halogenated unsymmetrical higher alkyl bisphenoxy alkane and an enhancing agent. The compositions of this invention preferably comprise about 50 to 90 percent ABS thermoplastic resin, about 5 to 30 percent halogenated unsymmetrical higher alkyl bisphenoxy alkane and about 0.1 to 15 percent enhancing agent, all by weight of the composition.

DETAILED DESCRIPTION OF THE PREERRED EMBODIMENTS

In accordance with this invention, halogenated unsymmetrical higher alkyl bisphenoxy alkanes are useful in the preparation of non-blooming flame retardant ABS resins. The novel compositions of this invention are distinguished from known flame retardant ABS compositions by improved properties.

Preferred novel flame retardant ABS compositions may be prepared by admixing from about 50% to about 90% by weight thermoplastic ABS resin; from about 5% to about 30% by weight halogented unsymmetrical higher alkyl bisphenoxy alkane compounds; from about 0.1% to about 15% by weight enhancing agent, where the percentages are based on the total weight of the resulting admixture of these three components. Most desirably, the compositions of this invention comprise about 60 to 90% ABS resin; about 10 to 30% halogenated unsymmetrical higher alkyl bisphenoxy alkane compound; and about 2 to 10% enhancing agent.

The ABS resin may be any thermoplastic resin formed by blending a styrene/acrylonitrile copolymer with butadiene-based rubber, or by grafing butadiene-based rubber with styrene/acrylonitrile chains; or by copolymerizing styrene, acrylonitrile and butadiene monomers. Thus, substantially any suitable acrylonitrile-butadiene-styrene composition may be used, containing each component of the terpolymer in substantially any proportion. The ABS may contain or may be substantially free of other additives such as stabilizers, plasticizers, dyes, pigments, fillers and the like.

Halogenated unsymmetrical higher alkyl bisphenoxy flame retardant additives in accordance with this invention are of the generalized structure:

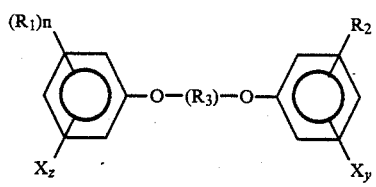

wherein X is bromine or chlorine; $R_1$ is a straight or branched $C_1$ to $C_{12}$ alkyl group; z is an integer from 2 to 5; n is 0, 1, or 2; $R_2$ is an alkyl selected from the groups consisting of sec-butyl (sec $C_4H_9$), pentyl ($C_5H_{11}$), hexyl ($C_6H_{13}$), heptyl ($C_7H_{15}$), octyl ($C_8H_{17}$), nonyl ($C_9H_{19}$), decyl ($C_{10}H_{21}$), undecyl ($C_{11}H_{23}$) and dodecyl ($C_{12}H_{25}$); y is 0 to 4; $R_3$ is a straight or branched $C_1$ to $C_{12}$ alkylene group; and such that if n is 1, $R_1$ is not $R_2$. The preferred additives may contain some minor amounts of symmetrical halogenated higher alkyl bisphenoxyl alkanes, which do not affect the utility of the composition as a nonblooming flame retardant agent. The especially preferred halogenated unsymmetrical higher alkyl bisphenoxy alkanes are described in the Borden, et al., copening United States Application Ser. No. 213,540 entitled "Halogenated Unsymmetrical Higher Alkyl Phenoxy Alkanes" filed June 30, 1988. The preferred additives are all unsymmetrical, that is $R_1$ is not $R_2$ where n is 1. The preferred additives in accordance with this invention include: 1-(Tribromophenoxy)-2-(dibromononylphenoxy)-ethane; 1-(tribromophenoxy)-2-(dibromooctylphenoxy)-ethane; 1-(tribromophenoxy)-2-(dibromopentylphenoxy)-ethane; 1-(tribromophenoxy)-2-(dibromododecylphenoxy)-ethane; 1-(tetrabromomethylphenoxy)-2-(dibromooctylphenoxy)-ethane; 1-(tetrabromomethylphenoxy)-2-(dibromononylphenoxy)-ethane; or 1-(pentabromophenoxy)-2-(dibromonomylphenoxy)-ethane.

The compositions of this invention also desirably incorporate one or more enhancing agents. Enhancing agents useful in accordance with this invention comprise the oxides and halides of groups IV-A and V-A of the periodic table; organic or inorganic compounds of phosphorous, nitrogen, boron or sulfur; and oxides and halides of, for example, zinc, magnesium and titanium, all as disclosed in U.S. Pat. No. 4,016,139. Preferred enhancing agents in accordance with this invention are the oxides of antimony, arsenic and bismuth, with the oxides of antimony being especially preferred. Antimony trioxide is the most preferred enhancing agent used in the compositions of this invention. As noted, the enhancing agent is supplied at the level of about 0.1-15 percent by weight. Preferably, the enhancing agent is used at a level of about 2-10 percent by weight.

The scope of the prsent invention includes the incorporation of other additives in the composition so far as to produce a particular end result. Such additives include, without limitation, heat stabilizers, light stabilizers, plasticizers, pigments, preservatives, ultraviolet light stabilizers, fillers, antioxidants, antistatic agents and other materials well known to those skilled in the art, for example, as described in *Modern Plastics Encyclopedia*, Vol. 63, No. 10A, McGraw-Hill, Inc. (1986).

EXAMPLES

The following preparations and examples are given to illustrate the invention and should not be construed as limiting its scope. All parts are by weight.

Example 1

A flame retardant composition was prepared by blending 20.0 parts halogenated unsymmetrical higher alkyl bisphenoxy alkane (Compound A); 69.0 parts ABS resin, which is available from Borg-Warner Corporation as CYCOLAC GSM 1000; 5.0 parts chlorinated polyethylene, which is available from The Dow Chemical Company as TYRIN CPE-4213S; 5.0 parts antimony trioxide, which is available from M & T Chemical Company as THERMOGUARD S; 0.5 parts stabilizer, which is available from Ciba Geigy Corporation as TINUVIN 770; and 0.5 parts antioxidant, which is available from Ciba Geigy Corporation as Irganox 1076.

Compound A is 1-(tribromophenoxy)-2-(dibromononylphenoxy)-ethane, an halogenated unsymmetrical higher alkyl bisphenoxy alkane prepared in accordance with Example 1 of the copending Borden, et al., patent application entitled [Halogenated Unsymmetrical Higher Alkyl Phenoxy Alkanes], filed herewith.

The resultant mixture was blended in a prep-center bowl (Model R6, C.W. Brabender Instruments, Inc., S. Hackensack, NJ) at 200° C. until a homogeneous mass developed. The admixture was cooled, ground into chips, and molded into test specimens. The chips were injection molded in a one-ounce injection molder (Model HI-30 RS, Newbury Industries, Inc., Newbury, OH). Conditions for injection molding are given in Table I. The resulting mixture had a bromine content of 10.8% by weight.

TABLE I

| INJECTION MOLDING MACHINE PARAMETERS | |
| --- | --- |
| Stock Temperature | 430° F. |
| Mold Temperature | 100° F. |
| Initial Ram Pressure | 1900 psi |
| Secondary Ram Pressure | 1000 psi |
| Total Injection Time | 5 sec |
| Cycle Time | 25 sec |

Bloom observations were made on molded test plaques which were aged at 70° C. for at least 2 to 6 weeks. Periodic visual inspections were used to detect the presence of deposits on the specimen surface.

EXAMPLES 2-7

Flame retardant compositions were prepared using the method of Example 2, except that Compound A was replaced by bis-phenoxy alkanes Compound B, Compound C, Compound D, Compound E, Compound G, and Compound I, respectively in proportion so as to maintain a 10.8 percent by weight bromine concentration in the resulting polymer composition. The identity for these compounds are listed in Table II.

TABLE II

| A | 1-(Tribromophenoxy)-2-(dibromononylphenoxy)-ethane |
| --- | --- |
| B | 1-(Tribromophenoxy)-2-(dibromooctylphenoxy)-ethane |
| C | 1-(Tribromophenoxy)-2-(dibromopentylphenoxy-ethane |
| D | 1-(Tribromophenoxy)-2-(dibromododecylphenoxy)-ethane |
| E | 1-(Tetrabromomethylphenoxy)-2-(dibromooctylphenoxy)-ethane |
| F | bis-(Dibromononylphenoxy)-ethane |
| G | 1-(Tetrabromomethylphenoxy)-2-(dibromononylphenoxy)-ethane |
| I | 1-(Pentabromophenoxy)-2-(dibromononylphenoxy)-ethane |
| J | bis-(Tribromophenoxy)-ethane |
| K | bis-(Tetrabromomethylphenoxy)-methane |
| L | bis-(Tribromophenoxy)-decane |

COMPARATIVE EXAMPLE 1-4

Flame retardant compositions were prepared using the method of Example 1, except that Compound A was replaced by Compound J, compound F, compound K, and Compound L, respectively in a proportion so as to maintain a 10.8 percent by weight bromine concentration in the resulting polymer composition. Identity for these Compounds J, F, K, and L. are listed in Table II.

Flame retardancy and physical properties of the various injected molded samples obtained from Examples 1–7 are reported in Table III which identifies the test procedures employed, all of which are well known to those skilled in the art.

TABLE III

| Example | Notched Izod ft-lb/in ASTM D-256 | Heat Deflec- °F. ASTM D-648 | Flamma- bility UL-94 | Tensile Strength psi ASTM D-638 | Elonga- tion % ASTM D-790 | Flexural Strength psi ASTM D-790 | Flexural Modulus $10^5$ psi ASTM D-790 |
| --- | --- | --- | --- | --- | --- | --- | --- |
| 1 | 4.2 | 156 | V-0 | 4800 | 40 | 7900 | 2.60 |
| 2 | 3.9 | 153 | V-0 | 5100 | 37 | 8400 | 2.80 |
| 3 | 4.1 | 151 | V-0 | 5500 | 21 | 9100 | 3.00 |
| 4 | 3.4 | 156 | V-0 | 4500 | 36 | 7400 | 2.50 |
| 5 | 3.7 | 156 | V-0 | 5200 | >30 | 8000 | 2.80 |
| 6 | 4.6 | 156 | V-0 | 4900 | 50 | 8100 | 2.70 |
| 7 | 4.9 | 158 | V-0 | 5100 | 55 | 8400 | 2.80 |
| Comp 1 | 2.5 | 151 | V-0 | 5400 | 12 | 9400 | 3.20 |
| Comp 2 | 3.8 | 140 | V-0 | 3300 | 4 | 3600 | 1.90 |
| Comp 3 | | | | | | | |
| Comp 4 | 4.0 | 150 | V-0 | 4800 | 52 | 8300 | 3.09 |

| Example | Melt Flow g/10 min ASTM D-1238 | Hardness R-Scale ASTM D-785 | Bloom 70°C. (See text) | Light Stabil- ity Delta E ASTM D-2565 | Yellow- ness Index initial ASTM D-1925 | Yellow- ness Index 300 hrs ASTM D-1925 |
| --- | --- | --- | --- | --- | --- | --- |
| 1 | 2.2 | 80 | No | 1.0 | 16.7 | 18.6 |
| 2 | 2.0 | 84 | No | 0.7 | 16.6 | 18.1 |
| 3 | 3.4 | 86 | No | | | |
| 4 | 2.3 | 73 | No | 1.3 | 17.2 | 20.0 |
| 5 | 2.0 | 73 | No | 0.2 | 16.2 | 16.4 |
| 6 | 2.3 | 84 | No | 3.8 | 17.0 | 25.2 |
| 7 | 1.8 | 85 | No | 6.0 | 17.0 | 30.0 |
| Comp 1 | 2.1 | 93 | Yes | 0.9 | 16.4 | 17.7 |
| Comp 2 | — | 36 | Yes | 0.3 | 17.6 | 17.8 |
| Comp 3 | | | Yes | | | |
| Comp 4 | 1.6 | 75 | Yes | 0.2 | | |

Table III shows the results of the experimental evaluations of various test specimens and may be summarized as follows.

Example 1 illustrates a flame retardant ABS formulation incorporating halogenated unsymmetrical higher alkyl bisphenoxy alkane in accordance with this invention. A flammability rating of V-O was achieved, and bloom was not obsreved.

Comparative Examples 1-show that prior art symmetrical bisphenoxy compound, when used in V-O formulaton, migrate (bloom) from ABS resin.

Examples 2-7 illustrate flame retardant formulations incorporating other halogenated unsymmetrical higher alkyl bisphenoxy alkanes within the scope of this invention.

It is especially important to note that ABS resins incorporating halogenated unsymmetrical higher alkyl bisphenoxy alkanes of this invention do not bloom whereas symmetrical bisphenoxy alkanes do bloom or tend to migrate from the resin compositions. It is to be noted that ABS resins incorporating the halogenated unsymmetrical higher alkyl bisphenoxy alkanes of this invention exhibit excellent resistance to light instability, to thermal migration of flame retarding agents, and have improved physical properties, such as impact strength and tensile elongation. cl EXAMPLES 8-10

Flame retardant compositions were prepared using the method of Example 1, except that Compound A was partially replaced by Compound J in proportion as specified in Table IV, so as to maintain a constant weight of bromine-containing flame retardant.

COMPARATIVE EXAMPLES 5-6

A flame retardant composition was prepared using the method of Eample 1, except that Compound A was replaced by compound J in proportion as specified in Table IV.

TABLE IV

| | BROMINE-CONTAINING COMPOUND, pbw | | |
|---|---|---|---|
| EXAMPLE | COMPOUND A | COMPOUND J | BLOOM |
| 1 | 20.0 | 0.0 | NO |
| 8 | 19.0 | 1.0 | NO |
| 9 | 18.0 | 2.0 | NO |
| 10 | 16.0 | 4.0 | NO |
| COMP 5 | 0.0 | 20.0 | YES |
| COMP 6 | 0.0 | 1.0 | YES |

Table IV shows the results of experimental evaluation of the various test specimens and may be summarized as follows:

Use of the halogenated unsymmetrical higher alkyl bisphenoxy alkanes of this invention in ABS resin formulations also suppresses bloom. In the case of bis(tribromophenoxy)-ethane (Compound J) severe bloom was noted in high (Comparative Example 5) and low (Comparative Example 6) loading levels. Examples 8-10 show no evidence of bloom in compositions comprising mixtures of the agents of this invention with bis(tribromophenoxy)-ethane (Compound J). Thus, the presence of Compound A retards or suppresses the blooming that would otherwise occur due to the presence of bis(tribromophenoxy)-ethane (Compound J).

We claim:

1. A non-blooming flame retardant acrylonitrile-butadiene-styrene resin composition comprising:
    a normally flammable acrylonitrile -butadienestyrene resin;
    as a flame retardant agent, an effective amount of halogenated unsymmetricalhigher alkyl bisphenoxy alkane to render the composition flame retardant;
    and
    a flame retardant enhancing agent wherein the halogenated unsymmetrical higher alkyl bisphenoxy alkane is a compound of the structure: wherein X is bromine or chlorine; $R_1$ is straight or branched alkyl from $C_1$ to $C_{12}$; z is an integer from 2 to 5; n is 0, 1, or 2; $R_2$ is straight or branched alkyl selected from the groups consisting of sec-butyl (sec $C_4H_9$), pentyl ($C_5H_{11}$), hexyl ($C_6H_{13}$), hpetyl ($C_7H_{15}$), octyl ($C_8H_{17}$), nonyl ($C_9H_{19}$), decyl ($C_{10}H_{21}$), undecyl ($C_{11}H_{23}$) and dodecyl ($C_{12}H_{25}$); y is 0, 1, or 2; $R_3$ is straight or branched alkylene from $C_1$ to $C_{12}$; and such that if n is 1, $R_1$ is not $R_2$.

2. A composition, as claimed in claim 1, wherein the composition comprises about 50 to about 90 percent ABS resin, about 5 to about 30 percent halogenated unsymmetrical higher alkyl bisphenoxy alkane and about 0.1 to about 15 percent enhancing agent, all by weight of the flame retardant ABS composition.

3. A composition, as claimed in claim 1 wherein the enhancing agent is selected from the group consisting of the oxides and halides of groups IV-A and V-A of the periodic table; organic or inorganic compounds of phosphorous, nitrogen, boron or sulfur; or oxides and halides of zinc, magnesium and titanium.

4. A composition as claimed in claim 1, wherein the enhancing agent is antimony trioxide.

5. A composition as claimed in claim 1, wherein the halogenated unsymmetrical higher alkyl bisphenoxy alkane is selected from the group consisting of: 1-(Tribromophenoxy)-2-(dibromononylphenoxy)-ethane; 1-(tribromophenoxy)-2-(dibromooctylphenoxy)-ethane; 1-(tribromophenoxy)-2-(dibromopentylphenoxy)-ethane; 1-(tribromophenoxy)-2-(dibromododecylphenoxy)-ethane; 1-(tetrabromomethylphenoxy)-2-(dibromooctylphenoxy)-ethane; 1-(tetrabromomethylphenoxy)-2-(dibromononylphenoxy)-ethane; 1-(pentabromophenoxy)-2-(dibromononylphenoxy)-ethane.

* * * * *

UNITED STATES PATENT AND TRADEMARK OFFICE
CERTIFICATE OF CORRECTION

PATENT NO. : 4,880,862  Page 1 of 2

DATED : November 14, 1989

INVENTOR(S) : Enrico J. Termine, Nicolai A. Favstritsky and Dennis M. Borden

It is certified that error appears in the above-identified patent and that said Letters Patent is hereby corrected as shown below: On the title page:

Inventor No. 2 should be -- Nicolai A. Favstritsky --;

Column 1, lines 4-5, "1. Field of the invention" should be flush with the left-hand margin;

Column 1, line 10, "2. Description of the Art" should be flush with the left-hand margin;

Column 1, line 45, add -- " -- before "Handbook";

Column 1, line 57, "agenst" should read -- agents --;

Column 2, line 67, "A" should read -- Z --;

Column 3, line 5, "$C_4 H_g$" should read -- $C_4 H_9$ --;

Column 3, line 28, "'b 710's" should read -- '710's --;

Column 4, line 23 "b isphenoxy" should read -- bisphenoxy --;

Column 5, line 7, "PREERRED" should read -- PREFERRED --;

Column 5, line 29, "grafing" should read -- grafting --;

Column 5, line 64, "copening" should read -- copending --;

Column 6, line 26, "prsent" should read -- present --;

Column 8, line 9, "compound F, compound K" should read -- Compound F, Compound K --;

UNITED STATES PATENT AND TRADEMARK OFFICE
CERTIFICATE OF CORRECTION

PATENT NO. : 4,880,862
DATED : November 14, 1989
INVENTOR(S) : Enrico J. Termine, Nicolai A. Favstritsky and Dennis M. Borden It is certified that error appears in the above-identified patent and that said Letters Patent is hereby corrected as shown below:

Column 8, line 58, "obsreved" should read -- observed --;

Column 8, line 61, "formulaton" should read -- formulation --;

Column 9, line 8, delete "cl" and center "EXAMPLES 8-10" on line 9;

Column 9, line 18, "Eample" should read -- Example --;

Column 9, line 19, "compound J" should read -- Compound J --;

Claim 1, line 3, butadienestyrene" should read -- butadiene-styrene --;

Claim 1, line 6, "unsymmetricalhigher" should read -- unsymmetrical higher --;

Claim 1, line 13, add the compound structure 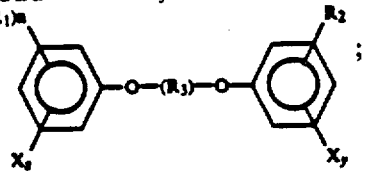 ;

Claim 1, line 17, "hpetyl" should read -- heptyl --.

Signed and Sealed this

Twenty-fourth Day of September, 1991

Attest:

HARRY F. MANBECK, JR.

*Attesting Officer*  *Commissioner of Patents and Trademarks*